US008889580B2

(12) United States Patent
Vermeiren et al.

(10) Patent No.: US 8,889,580 B2
(45) Date of Patent: Nov. 18, 2014

(54) MIXTURES OF MOLECULAR SIEVES COMPRISING MEAPO, THEIR USE IN CONVERSION OF ORGANICS TO OLEFINS

(75) Inventors: Walter Vermeiren, Houthalen (BE); Nikolai Nesterenko, Nivelles (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 925 days.

(21) Appl. No.: 12/671,218

(22) PCT Filed: Jul. 28, 2008

(86) PCT No.: PCT/EP2008/059884
§ 371 (c)(1),
(2), (4) Date: Jun. 18, 2010

(87) PCT Pub. No.: WO2009/016154
PCT Pub. Date: Feb. 5, 2009

(65) Prior Publication Data
US 2010/0256316 A1    Oct. 7, 2010

(30) Foreign Application Priority Data
Jul. 31, 2007   (EP) .................................... 07113546

(51) Int. Cl.
*B01J 29/06* (2006.01)
*C07C 1/00* (2006.01)
*C07C 1/20* (2006.01)
*C07C 1/32* (2006.01)
*B01J 29/00* (2006.01)
*B01J 29/035* (2006.01)
*B01J 29/85* (2006.01)
*B01J 29/84* (2006.01)

(52) U.S. Cl.
CPC . *C07C 1/20* (2013.01); *C07C 1/322* (2013.01); *B01J 29/035* (2013.01); *B01J 29/005* (2013.01); *B01J 29/85* (2013.01); *B01J 29/84* (2013.01)
USPC ................ 502/67; 502/64; 502/66; 502/69; 502/71; 585/314; 585/315; 585/324; 585/326; 585/642

(58) Field of Classification Search
USPC ............ 502/64, 66, 67, 69, 71; 585/638, 639, 585/640, 641, 642, 314, 315, 324, 326, 327, 585/329
See application file for complete search history.

(56) References Cited

U.S. PATENT DOCUMENTS

| 4,803,184 | A | * | 2/1989 | Long et al. ....................... 502/63 |
| 4,818,739 | A | * | 4/1989 | Gortsema et al. ............... 502/67 |
| 4,857,495 | A | * | 8/1989 | Gortsema et al. ............. 502/214 |
| 4,859,314 | A | * | 8/1989 | Pellet et al. ................... 208/114 |
| 4,867,861 | A | * | 9/1989 | Abdo et al. ...................... 208/27 |
| 4,880,760 | A | * | 11/1989 | Pellet et al. ..................... 502/67 |
| 6,080,303 | A | * | 6/2000 | Cao et al. ................. 208/120.01 |
| 6,150,293 | A | * | 11/2000 | Verduijn et al. ................ 502/67 |
| 6,372,680 | B1 | * | 4/2002 | Wu et al. ......................... 502/64 |
| 6,504,074 | B2 | * | 1/2003 | Verduijn et al. .............. 585/475 |
| 6,812,181 | B2 | * | 11/2004 | van der Berge et al. ........ 502/67 |
| 2002/0082460 | A1 | * | 6/2002 | Verduijn et al. .............. 585/475 |
| 2002/0099249 | A1 | * | 7/2002 | Drake et al. .................. 585/408 |
| 2004/0048734 | A1 | * | 3/2004 | Liu et al. ......................... 502/64 |
| 2004/0064008 | A1 | * | 4/2004 | Maurer et al. ................. 585/640 |
| 2004/0266608 | A1 | * | 12/2004 | Long et al. ....................... 502/68 |
| 2005/0070422 | A1 | | 3/2005 | Chen et al. |
| 2005/0096214 | A1 | | 5/2005 | Janssen et al. |
| 2005/0202963 | A1 | * | 9/2005 | Levin et al. ................... 502/214 |
| 2005/0234279 | A1 | * | 10/2005 | Serra et al. .................... 585/475 |
| 2005/0245781 | A1 | * | 11/2005 | Martens et al. ............... 585/640 |
| 2006/0063956 | A1 | | 3/2006 | Kalnes et al. |
| 2006/0079397 | A1 | | 4/2006 | Mertens et al. |
| 2006/0100471 | A1 | * | 5/2006 | Serra Alfaro et al. ......... 585/475 |
| 2006/0161035 | A1 | | 7/2006 | Kalnes et al. |
| 2006/0195001 | A1 | | 8/2006 | Coute et al. |
| 2007/0043250 | A1 | * | 2/2007 | Xu et al. ........................ 585/639 |

FOREIGN PATENT DOCUMENTS

WO          0160770 A      8/2001

* cited by examiner

*Primary Examiner* — Elizabeth Wood

(57) ABSTRACT

The present invention is a mixture comprising by weight 0.01 to 28% of at least one medium or large pore crystalline silicoaluminate, silicoaluminophosphate materials or silicoaluminate mesoporous molecular sieves (co-catalyst) (A) for respectively 99.99 to 72% of at least a MeAPO molecular sieve.
Preferably the proportion of (A) is 1 to 15% for respectively 99 to 85% of MeAPO molecular sieves.
MeAPO molecular sieves having CHA (SAPO-34) or AEI (SAPO-18) structure or mixture thereof are the most preferable. Si is the most desirable metal in MeAPO.
The present invention also relates to catalysts consisting of the above mixture or comprising the above mixture.
The present invention also relates to a process (hereunder referred as "XTO process") for making an olefin product from an oxygen-containing, halogenide-containing or sulphur-containing organic feedstock wherein said oxygen-containing, halogenide-containing or sulphur-containing organic feedstock is contacted with the above catalyst (in the XTO reactor) under conditions effective to convert the oxygen-containing, halogenide-containing or sulphur-containing organic feedstock to olefin products (the XTO reactor effluent).
The present invention also relates to a process (hereunder referred as "combined XTO and OCP process") to make light olefins from an oxygen-containing, halogenide-containing or sulphur-containing organic feedstock comprising:
contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;
separating said light olefins from said heavy hydrocarbon fraction;
contacting said heavy hydrocarbon fraction in the OCP reactor at conditions effective to convert at least a portion of said heavy hydrocarbon fraction to light olefins.

28 Claims, 2 Drawing Sheets

US 8,889,580 B2

MIXTURES OF MOLECULAR SIEVES COMPRISING MEAPO, THEIR USE IN CONVERSION OF ORGANICS TO OLEFINS

FIELD OF THE INVENTION

The present invention relates to mixtures of molecular sieves comprising MeAPO as well as their use in conversion of organics to olefins. More precisely the invention is a mixture comprising MeAPO and a crystalline silicoaluminate or silicate molecular sieve. These crystalline silicoaluminate or silicate molecular sieve have medium or large pore size as compared with the small pore size of the MeAPO. The mixtures of the invention are useful as catalysts in a variety of processes including cracking, hydrocracking, isomerization, reforming, dewaxing, alkylation, transalkylation, conversion of oxygenates (or halogenide-containing or sulphur-containing organic compounds) to light olefins.

The limited supply and increasing cost of crude oil has prompted the search for alternative processes for producing hydrocarbon products. One such process is the conversion of oxygen-containing (by way of example methanol), halogenide-containing or sulphur-containing organic compounds to hydrocarbons and especially light olefins (by light olefins is meant $C_2$ to $C_4$ olefins) or gasoline and aromatics. In the present application the conversion of said oxygen-containing (also referred as oxygenates), halogenide-containing or sulphur-containing organic compounds to hydrocarbons and especially light olefins is referred as XTO process. The interest in the XTO process is based on the fact that feedstock's, especially methanol can be obtained from coal, biomass, organic waste or natural gas by the production of synthesis gas which is then processed to produce methanol. The XTO process can be combined with an OCP (olefins cracking process) process to increase production of olefins. The XTO process produces light olefins such as ethylene and propylene as well as heavy hydrocarbons such as butenes and above. These heavy hydrocarbons are cracked in an OCP process to give mainly ethylene and propylene.

BACKGROUND OF THE INVENTION

US20060106270A1 relates to a process wherein the average propylene cycle selectivity of an oxygenate to propylene (OTP) process using a dual-function oxygenate conversion catalyst is substantially enhanced by the use of a combination of: 1) moving bed reactor technology in the hydrocarbon synthesis portion of the OTP flow scheme in lieu of the fixed bed technology of the prior art; 2) a hydrothermally stabilized and dual-functional catalyst system comprising a molecular sieve having dual-function capability dispersed in a phosphorus-modified alumina matrix containing labile phosphorus and/or aluminum anions; and 3) a catalyst on-stream cycle time of 400 hours or less. The use of a mixture of a zeolitic catalyst system with a non-zeolitic catalyst system is described. This mixed catalyst embodiment can be accomplished either using a physical mixture of particles containing the zeolitic material with particles containing the non-zeolitic material or the catalyst can be formulated by mixing the two types of material into the phosphorus modified aluminum matrix in order to form particles having both ingredients present therein. In either case the preferred combination is a mixture of ZSM-5 or ZSM-11 with SAPO-34 in relative amounts such that ZSM-5 or ZSM-11 comprises 30 to 95 wt % of the molecular sieve portion of the mixture with a value of about 50 to 90 wt % being especially preferred.

US20060063956A1 relates to a process wherein the average cycle propylene selectivity of an oxygenate to propylene (OTP) process using one or more fixed or moving beds of a dual-function oxygenate conversion catalyst with recycle of one or more C4+ olefin-rich fractions is substantially enhanced by the use of selective hydrotreating technology on these C4+ olefin-rich recycle streams to substantially eliminate detrimental coke precursors such as dienes and acetylenic hydrocarbons. This hydrotreating step helps hold the build-up of detrimental coke deposits on the catalyst to a level which does not substantially degrade dual-function catalyst activity, oxygenate conversion and propylene selectivity, thereby enabling a substantial improvement in propylene average cycle yield. The propylene average cycle yield improvement enabled by the present invention over that achieved by the prior art using the same or a similar catalyst system but without the use of the hydrotreating step on the C4+ olefin-rich recycle stream is of the order of about 1.5 to 5.5 wt-% or more. The preferred combination is a mixture of ZSM-5 with SAPO-34 in relative amounts such that SAPO-34 comprises 30 to 70 wt % of the molecular sieve portion of the mixture with a value of about 45 to 55 wt % being especially preferred.

U.S. Pat. No. 6,051,746 describes oxygenate conversions using modified small pore molecular sieve catalysts. The invention relates to a process for converting oxygenated organic material, to olefins using small pore molecular sieve catalysts. More particularly, the invention relates to a method for converting oxygenated organic material to olefins with improved the olefin yields and decreased yields of methane and other light saturate byproducts. The improved yield slate is achieved by treating the small pore molecular sieve catalyst with a modifier selected from the group consisting of polynuclear aromatic heterocyclic compounds with at least three interconnected ring structures having at least one nitrogen atom as a ring substituent, each ring structure having at least five ring members, decomposed derivatives of said polynuclear aromatic heterocyclic compound, and mixtures thereof.

US20060195001A1 describes combinations of molecular sieve catalysts to provide a catalyst mixture having a beneficial combination of the activities and selectivities of the individual molecular sieves. The molecular sieve catalysts can be formulated or unformulated silicoaluminophosphate molecular sieves, silicoaluminate molecular sieves, and/or metalloaluminophosphate molecular sieves. In particular, said application relates to mixtures of molecular sieves for use as catalysts in converting oxygenates such as methanol to olefins. At [0113] and [0114] on page 10 are described mixtures of SAPO-34 and AEI/CHA intergrowth material having a Si:Al ratio of roughly 0.06. As explained in [0065] AEI and CHA are respectively the structure of SAPO-18 and SAPO-34.

U.S. Pat. No. 6,951,830B2 relates to a catalyst composition, a method of making the same and its use in the conversion of a feedstock, preferably an oxygenated feedstock, into one or more olefin(s), preferably ethylene and/or propylene The catalyst composition comprises a molecular sieve, such as a silicoaluminophosphate and/or an aluminophosphate, hydrotalcite, and optionally a rare earth metal component.

US20070043250A1 describes an oxygenate conversion catalyst useful in the conversion of oxygenates such as methanol to olefinic products which is improved by the use of a catalyst combination based on a molecular sieve in combination with a co-catalyst comprising a mixed metal oxide composition which has oxidation/reduction functionality under the conditions of the conversion. This metal oxide co-catalyst component will comprise a mixed oxide of one or more, preferably at least two, transition metals, usually of Series 4, 5 or 6 of the Periodic Table, with the metals of Series 4 being preferred, as an essential component of the mixed oxide composition. The preferred transition metals are those of Groups 5, especially titanium and vanadium, Group 6, especially chromium or molybdenum, Group 7, especially manganese and Group 8, especially cobalt or nickel. Other metal oxides may also be present. The preferred molecular sieve components in these catalysts are the high silica zeolites and the SAPOs, especially the small pore SAPOs (8-membered rings), such as SAPO-34. These catalyst combinations exhibit reduced coke selectivity have the potential of achieving extended catalyst life. In addition, these catalysts have the capability of selectively converting the hydrogen produced during the conversion to liquid products, mainly water, reducing the demand on reactor volume and product handling.

Small pore silicoaluminophosphate (SAPO) molecular sieve catalysts have excellent selectivity in oxygenates to light olefin reactions. However, these catalysts have a tendency to deactivate rapidly during the conversion of oxygenates to olefins and the ratio C3/C2 could be improved. Therefore a need exists for methods to decrease the rate of deactivation of small pore zeolitic catalysts during such conversions and to improve the C3/C2 ratio.

It has been discovered that addition of a small amount of medium or large pore crystalline silicoaluminate, silicoaluminophosphate materials or silicoaluminate mesoporous molecular sieves to a small pore MeAPO molecular sieve based catalyst leads to substantial increase of C3/C2 ratio, C4+ yield and stability in XTO than was obtained over parent molecular sieve (MeAPO).

Higher stability of blended catalysts provides a possibility to operate at higher flow rate, increase the catalyst on-stream time in XTO conversion reactor and decrease the size of regeneration section or the frequency of regeneration. (on-stream time is the time that a catalyst resides in the conversion reactor and exhibits still sufficient catalytic activity, before it has to be taken off-line for regeneration or replacement)

Unexpectedly, this blended catalysts possesses reduced coke selectivity in comparison with the weighted average of the individual molecular sieves.

The excess of C4+ as well as ethylene can be converted to propylene in an olefin cracking fixed bed reactor (OCP) in combination with the XTO process. Ethylene can be recycled back in XTO reactor or to the OCP reactor. The excess C4+ as well as the ethylene can be converted to more propylene by recycling C4+ and ethylene back to the XTO reactor. The catalyst blend allows the conversion of organic compounds, C4+ and ethylene at the same time.

Stated above small pore MeAPO molecular sieves contain 8 members ring as a largest pore aperture in the structure, medium pore crystalline silicoaluminates contain 10 members ring as a largest pore aperture, large pore crystalline silicoaluminates contain 12 members ring in the structure. Stated above medium, large pore and mesoporous molecular sieves have acid properties and could catalyse the formation of aromatic precursor from used feedstock.

In the XTO process the ethylene, propylene and higher hydrocarbons are formed via a "carbon pool" mechanism. Ethylene, propylene and C4+ olefins selectivities in XTO process are related to the number of methyl groups attached to benzene rings trapped in the nanocages. The product spectrum varies strongly with the pore size of the catalytic material (shape selectivity), and when the small pore SAPO-34 (chabasite structure) is used as catalyst the hydrocarbon products are mostly ethene and propene, and some substantially linear butenes, the only product molecules small enough to escape with ease through the narrow pores.

It has been discovered that medium or large pore crystalline silicoaluminate, silicoaluminophosphate materials or silicoaluminate mesoporous molecular sieves play a role of a faster in-situ supply for aromatics precursor for olefins production by carbon pool mechanism. One object of this invention is in-situ on-purpose formation of some additional organic reaction centers by adding to the MeAPO a small amount of acid co-catalyst with larger pore opening than the MeAPO. These materials are capable to produce a small amount of higher molecular weight precursors that can enter into the pore system of the small pore MeAPO where they are converted into the aromatics under XTO conditions. These aromatics constitute the active centers for XTO according to the carbon pool mechanism. These aromatics are trapped by MeAPO micro porous system in a more optimum way without formation of a lot of coke by-products. This allows increasing of catalyst stability and C3/C2 ratio.

Without being bonded by an explanation, inventors think that an optimum concentration of the methylbenzenes organic reaction centers leads to higher light olefins production and to a slower deactivation. However the olefins production is limited by diffusion of heavy olefins out of the micropore system of MeAPO in which usually methylbenzenes are trapped. Formation of the methylbenzenes inside of MeAPO pore system requires a certain time and is accompanied by coke formation. More coke formation in the small pore MeAPO reduces the accessible pore volume and results in faster loss of catalytic activity.

BRIEF DESCRIPTION OF THE INVENTION

The present invention is a mixture comprising by weight 0.01 to 28% of at least one medium or large pore crystalline silicoaluminate, silicoaluminophosphate materials or silicoaluminate mesoporous molecular sieves (co-catalyst) (A) for respectively 99.99 to 72% of at least a small pore MeAPO molecular sieve.

Advantageously the proportion of (A) is 0.5 to 28% for respectively 99.5 to 72% of small pore MeAPO molecular sieves.

More advantageously the proportion of (A) is 0.5 to 25% for respectively 99.5 to 75% of small pore MeAPO molecular sieves.

Preferably the proportion of (A) is 1 to 15% for respectively 99 to 85% of small pore MeAPO molecular sieves. More preferably the proportion of (A) is 3 to 15% for respectively 97 to 85% of small pore MeAPO molecular sieves.

MFI, FER and MEL are the most preferable medium pore crystalline silicoaluminates.

AEL is the most preferable medium pore silicoaluminophosphate material.

FAU, MOR, LTL, MAZ, MWW and BEA are the most preferable large pore crystalline silicoaluminates.

AFI is the most preferable large pore silicoaluminophosphate materials,

MCM-41 is the most preferable mesoporous molecular sieve.

MeAPO's have a three-dimensional microporous crystal framework of $PO_2^+$, $AlO_2^-$, and $MeO_2$ tetrahedral units. MeAPO molecular sieves having CHA (SAPO-34, SAPO-44) or AEI (SAPO-18) structure or mixture thereof are the most preferable. Si is the most desirable metal in MeAPO.

According to another embodiment of the invention the MeAPO molecular sieve has an empirical chemical composition on an anhydrous basis, after synthesis and calcination, expressed by the formula $H_xMe_yAl_zP_kO_2$ in which, $$y+z+k=1$$

$$x<=y$$

y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54

Advantageously said molecular sieve have predominantly a plate crystal morphology. Preferably said plate crystal morphology is such as the width (W) and the thickness (T) are as follows:

W/T is >=10 and advantageously ranges from 10 to 100.

According to another embodiment of the invention the MeAPO has been prepared by a method comprising:
a) forming a reaction mixture containing a texture influencing agent (TIA), an organic templating agent (TEMP), at least a reactive inorganic source of $MeO_2$ essentially insoluble in the TIA, reactive sources of $Al_2 O_3$ and $P_2 O_5$,
b) crystallizing the above reaction mixture thus formed until crystals of the metalloaluminophosphate are formed,
c) recovering a solid reaction product,
d) washing it with water to remove the TIA and
e) calcinating it to remove the organic template.

The present invention also relates to catalysts consisting of the above mixture or comprising the above mixture.

The present invention also relates to a process (hereunder referred as "XTO process") for making an olefin product from an oxygen-containing, halogenide-containing or sulphur-containing organic feedstock wherein said oxygen-containing, halogenide-containing or sulphur-containing organic feedstock is contacted with the above catalyst (in the XTO reactor) under conditions effective to convert at least a portion of the oxygen-containing, halogenide-containing or sulphur-containing organic feedstock to olefin products (the XTO reactor effluent). It is desirable to have a substantially 100% conversion of the organic compound in the XTO reactor. This conversion rate is adjusted by optimization of contact time and the frequency of regeneration of the catalyst.

According to a specific embodiment the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionated to form a stream comprising essentially ethylene and at least a part of said stream is recycled in the XTO reactor to increase the propylene production and then the flexibility of ethylene vs propylene production.

According to another embodiment of the invention both ethylene and the C4+ can be recycled in the XTO reactor.

The present invention also relates to a process (hereunder referred as "combined XTO and OCP process") to make light olefins from an oxygen-containing, halogenide-containing or sulphur-containing organic feedstock comprising:

contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;

separating said light olefins from said heavy hydrocarbon fraction;

contacting said heavy hydrocarbon fraction in the OCP reactor at conditions effective to convert at least a portion of said heavy hydrocarbon fraction to light olefins. It is desirable to have a substantially 100% conversion of the organic compound in the XTO reactor. This conversion rate is adjusted by optimization of contact time and the frequency of regeneration of the catalyst.

DETAILED DESCRIPTION OF THE INVENTION

Figure 1:
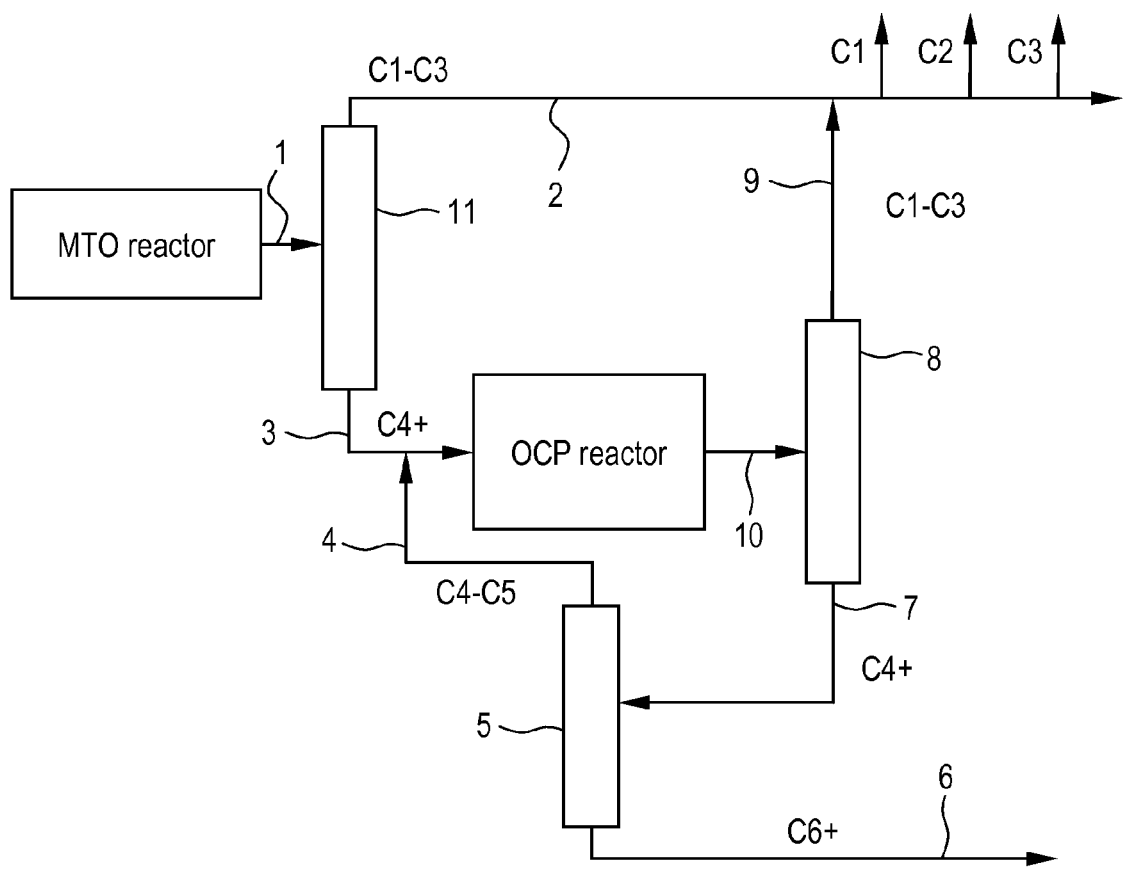
FIG. 1 depicts an arrangement of an XTO reactor and OCP reactor in accordance with one or more embodiments.

As regards (A), among the products which may be used, they include MFI, MEL, FER, MOR, FAU, BEA, AEL, AFI, LTL, MAZ, MWW and MCM-41. Preferably they have pore apertures defined by 10 or 12 tetrahedric atoms and 10 or 12 oxygen atoms. The most preferably they are of the MFI (ZSM-5 or silicalite), FAU, MOR, MEL or FER type. Zeolites may be pretreated by various ways, modified by P, by alkali, alkali-earth and/or rare-earth metals. Pretreatment may be carried our by acid leaching, steaming or combination thereof.

Advantageously (A) is a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D and silicalite-2 as described by the International Zeolite Association (*Atlas of Zeolite Structure Types*, 1987, Butterworths).

Crystalline silicates are microporous crystalline inorganic polymers based on a framework of $XO_4$ tetrahydra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]: 0.51-0.55 nm. Crystalline silicates with the MEL structure possess a bi-directional intersecting straight pore system with straight channels along [100] having pore diameters of 0.53-0.54 nm.

The MFI or MEL catalyst having a high silicon/aluminum atomic ratio may be manufactured by removing aluminum from a commercially available crystalline silicate. A typical commercially available silicalite has a silicon/aluminum atomic ratio of around 120 to 300. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The framework silicon/aluminum ratio may be increased by this process to a value of at least about 180, preferably from about 180 to 1000, more preferably at least 200, yet more preferably at least 300 and most preferably around 480.

As regards the MeAPO, they are known per se. MeAPO are described in U.S. Pat. No. 4,440,871, U.S. Pat. No. 6,207,872, U.S. Pat. No. 6,540,970 and U.S. Pat. No. 6,303,534, the content of which are enclosed in the present application. In an advantageous embodiment the MeAPO molecular sieves have essentially a structure CHA or AEI or a mixture thereof. Preferably they have essentially the structure SAPO 18 or SAPO 34 or a mixture thereof.

About "essentially" referring to the CHA or AEI structure it means that advantageously more than 80% by weight, preferably more than 90%, of the MeAPO has the structure CHA or AEI or a mixture thereof. About "essentially" referring to the SAPO 18 or SAPO 34 structure it means that advantageously more than 80% by weight, preferably more than 90%, of the MeAPO has the structure SAPO 18 or SAPO 34 or a mixture thereof.

Me is advantageously a metal selected from the group consisting of silicon, germanium, magnesium, zinc, iron, cobalt, nickel, manganese, chromium and mixtures thereof. Preferred metals are silicon, magnesium and cobalt with silicon or germanium being especially preferred.

The MeAPO could be also an intergrown phase of two MeAPO having AEI and CHA framework types. They are described in U.S. Pat. No. 7,067,095, U.S. Pat. No. 6,953,767 and U.S. Pat. No. 6,334,994, the content of which are enclosed in the present application.

As regards the MeAPO, according to another embodiment of the invention the MeAPO molecular sieve has an empirical chemical composition on an anhydrous basis, after synthesis and calcination, expressed by the formula $H_xMe_yAl_zP_kO_2$ in which, $y+z+k=1$ $x<=y$ y has a value ranging from 0.0008 to 0.4 and advantageously from 0.005 to 0.18 z has a value ranging from 0.25 to 0.67 and advantageously from 0.38 to 0.55 k has a value ranging from 0.2 to 0.67 and advantageously from 0.36 to 0.54

In a advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

In an advantageous embodiment the MeAPO molecular sieves have essentially a structure CHA or AEI or a mixture thereof. Preferably they have essentially the structure SAPO 18 or SAPO 34 or a mixture thereof.

Advantageously said molecular sieve have predominantly a plate crystal morphology. Preferably said plate crystal morphology is such as the width (W) and the thickness (T) are as follows:

W/T is >=10 and advantageously ranges from 10 to 100.

In a preferred embodiment T is <=0.15 μm, more desirably <=0.10 μm, more desirably <=0.08 μm, advantageously ranges from 0.01 to 0.07 μm and preferably from 0.04 to 0.07 μm.

About the plate crystal morphology, said plates have advantageously the shape of a simple polygon comprised in a square. The square's length is named W. The MeAPO molecular sieves have predominantly a plate crystal morphology. By predominantly is meant advantageously greater than 50% of the crystals. Preferably at least 70% of the crystals have a plate morphology and most preferably at least 90% of the crystals have a plate morphology. About "essentially" referring to the CHA or AEI structure it means that advantageously more than 80% by weight, preferably more than 90%, of the MeAPO of the invention has the structure CHA or AEI or a mixture thereof. About "essentially" referring to the SAPO 18 or SAPO 34 structure it means that advantageously more than 80% by weight, preferably more than 90%, of the MeAPO has the structure SAPO 18 or SAPO 34 or a mixture thereof.

With regards to a method to make said MeAPO, it can be made by a method which comprises:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$, said reaction mixture having a composition expressed in terms of molar oxide ratios of:

TEMP/$Al_2O_3$=0.3-5, more desirable 0.5-2

$MeO_2$/$Al_2O_3$=0.005-2.0, more desirable 0.022-0.8

$P_2O_5$/$Al_2O_3$=0.5-2, more desirable 0.8-1.2

TIA/$Al_2O_3$=3-30, more desirable 6-20 b) crystallizing the above reaction mixture thus formed until crystals of the metalloaluminophosphate are formed, c) recovering a solid reaction product, d) washing it with water to remove the TIA and e) calcinating it to remove the organic template.

In an advantageous embodiment TEMP/$Al_2O_3$=0.5-2; $MeO_2$/$Al_2O_3$=0.022-0.8; $P_2O_5$/$Al_2O_3$=0.8-1.2 and TIA/$Al_2O_3$=6-20.

In a first preferred embodiment $TEMP/Al_2O_3=0.5$-$2$; $MeO_2/Al_2O_3=0.022$-$0.7$; $P_2O_5/Al_2O_3=0.8$-$1.2$ and $TIA/Al_2O_3=6$-$20$.

In a second preferred embodiment $TEMP/Al_2O_3=0.7$-$2$; $MeO_2/Al_2O_3=0.05$-$0.7$; $P_2O_5/Al_2O_3=0.8$-$1.2$ and $TIA/Al_2O_3=6$-$20$.

In a third preferred embodiment $TEMP/Al_2O_3=0.7$-$2$; $MeO_2/Al_2O_3=0.05$-$0.6$; $P_2O_5/Al_2O_3=0.8$-$1.2$ and $TIA/Al_2O_3=6$-$20$.

With regards to the TIA, mention may be made, by way of example, of 1,2-propanediol, 1,3-propanediol, methanol, ethanol, propanol, isopropanol, butanol, glycerol or ethylene glycol.

With regards to the organic templating agent, it can be any of those heretofore proposed for use in the synthesis of conventional zeolitic aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]$, wherein "x" has a value of at least 2 are also suitably employed. Both mono-, di and tri-amines are advantageously utilized, either alone or in combination with a quaternary ammonium compound or other templating compound. Representative templating agents include tetramethylammonium, tetraethylammonium, tetrapropylammonium or tetrabutylammonium cations; di-n-propylamine, tripropylamine, triethylamine; diethylamine, triethanolamine; piperidine; morpholine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo(2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Advantageously organic templating agent is selected among tetraethylammonium hydroxide (TEAOH), diisopropylethylamine (DPEA), tetraethyl ammonium salts, cyclopentylamine, aminomethyl cyclohexane, piperidine, triethylamine, diethylamine, cyclohexylamine, triethyl hydroxyethylamine, morpholine, dipropylamine, pyridine, isopropylamine di-n-propylamine, tetra-n-butylammonium hydroxide, diisopropylamine, di-n-propylamine, n-butylethylamine, di-n-butylamine, and di-n-pentylamine and combinations thereof. Preferably the template, is a tetraethyl ammonium compound selected from the group of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Most preferably, the template is tetraethyl ammonium hydroxide.

With regards to the reactive inorganic source of $MeO_2$ essentially insoluble in the TIA and relating to silicon, non-limiting examples of useful inorganic silicon source materials non-soluble in alcohols include, fumed silica, aerosol, pyrogenic silica, precipitated silica and silica gel.

With regards to the reactive sources of $Al_2O_3$, it can be any aluminum species capable of being dispersed or dissolved in an aqueous synthesis solution. Useful sources of alumina are one or more sources selected from the group consisting of the following: hydrated alumina, organo alumina, in particularly $Al(OiPr)_3$, pseudo-boehmite, aluminum hydroxide, colloidal alumina, aluminium halides, aluminium carboxylates, aluminium sulfates and mixtures thereof.

With regards to the reactive sources of $P_2O_5$, it can be one or more sources selected from the group consisting of phosphoric acid; organic phosphates, such as triethyl phosphate, tetraethyl-ammonium phosphate; aluminophosphates; and mixtures thereof. The phosphorous source should also be capable of being dispersed or dissolved in an alcohol synthesis solution.

These MeAPO can be prepared by the usual methods of the molecular sieves synthesis technology provided it is in accordance with the above cited ratios. The reaction mixture is in the form of a gel. The ratios $MeO_2/Al_2O_3$ and $P_2O_5/Al_2O_3$ are selected among the above described advantageous and preferred ratios and are in accordance with the advantageous and preferred y, z and k described above. By way of example to make a MeAPO having the y, z and k according to the second preferred embodiment one has to use the ratios of the ingredients according to the second preferred embodiment of the method to make said MeAPO.

With regards to the step b), the reaction mixture obtained by mixing the reactive sources of alumina, $MeO_2$, phosphorus, organic templating agent and TIA is submitted to autogenous pressure and elevated temperature. The reaction mixture is heated up to the crystallization temperature that may range from about 120° C. to 250° C., preferably from 130° C. to 225° C., most preferably from 150° C. to 200° C. Heating up to the crystallization temperature is typically carried for a period of time ranging from about 0.5 to about 16 hours, preferably from about 1 to 12 hours, most preferably from about 2 to 9 hours. The temperature may be increased stepwise or continuously. However, continuous heating is preferred. The reaction mixture may be kept static or agitated by means of tumbling or stirring the reaction vessel during hydrothermal treatment. Preferably, the reaction mixture is tumbled or stirred, most preferably stirred. The temperature is then maintained at the crystallization temperature for a period of time ranging from 2 to 200 hours. Heat and agitation is applied for a period of time effective to form crystalline product. In a specific embodiment, the reaction mixture is kept at the crystallization temperature for a period of from 16 to 96 hours.

With regards to the step c), the usual means can be used. Typically, the crystalline molecular sieve product is formed as a slurry and can be recovered by standard means, such as by sedimentation, centrifugation or filtration.

With regards to the step d), the separated molecular sieve product is washed, recovered by sedimentation, centrifugation or filtration and dried.

With regards to the step e), calcination of molecular sieves is known per se. As a result of the molecular sieve crystallization process, the recovered molecular sieve contains within its pores at least a portion of the template used. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system.

Additionally, if during the synthesis alkaline or alkaline earth metals have been used, the molecular sieve might be subjected to an ion-exchange step. Conventionally, ion-exchange is done in aqueous solutions using ammonium salts or inorganic acids.

As regards the MeAPO and according to another embodiment of the invention the MeAPO has been prepared by a method comprising:

a) forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$,
b) crystallizing the above reaction mixture thus formed until crystals of the metalloaluminophosphate are formed,
c) recovering a solid reaction product,
d) washing it with water to remove the TIA and
e) calcinating it to remove the organic template.

In a usual embodiment said reaction mixture has a composition expressed in terms of molar oxide ratios of:
$TEMP/Al_2O_3$=0.3-5, more desirable 0.5-2
$MeO_2/Al_2O_3$=0.005-2.0, more desirable 0.022-0.8
$P_2O_5/Al_2O_3$=0.5-2, more desirable 0.8-1.2
$TIA/Al_2O_3$=3-30, more desirable 6-20

In an advantageous embodiment $TEMP/Al_2O_3$=0.5-2; $MeO_2/Al_2O_3$=0.022-0.8; $P_2O_5/Al_2O_3$=0.8-1.2 and $TIA/Al_2O_3$=6-20.

In a first preferred embodiment $TEMP/Al_2O_3$=0.5-2; $MeO_2/Al_2O_3$=0.022-0.7; $P_2O_5/Al_2O_3$=0.8-1.2 and $TIA/Al_2O_3$=6-20.

In a second preferred embodiment $TEMP/Al_2O_3$=0.7-2; $MeO_2/Al_2O_3$=0.05-0.7; $P_2O_5/Al_2O_3$=0.8-1.2 and $TIA/Al_2O_3$=6-20.

In a third preferred embodiment $TEMP/Al_2O_3$=0.7-2; $MeO_2/Al_2O_3$=0.05-0.6; $P_2O_5/Al_2O_3$=0.8-1.2 and $TIA/Al_2O_3$=6-20.

In a usual embodiment the metalloaluminophosphate (MeAPO) molecular sieves made with the above method have a lamellar crystal morphology having an empirical chemical composition on an anhydrous basis, after synthesis and calcination, expressed by the formula $H_xMe_yAl_zP_kO_2$ wherein, $$y+z+k=1$$

$$x<=y$$

y has a value ranging from 0.0008 to 0.4 and more desirable from 0.005 to 0.18
z has a value ranging from 0.25 to 0.67 and more desirable from 0.38 to 0.55
k has a value ranging from 0.2 to 0.67 and more desirable from 0.36 to 0.54
said molecular sieve having predominantly a plate crystal morphology.

The values of y, z and k in the usual embodiment are obtained by the ratios of the ingredients described in the usual embodiment method above described.

In an advantageous embodiment y has a value ranging from 0.005 to 0.18, z has a value ranging from 0.38 to 0.55 and k has a value ranging from 0.36 to 0.54.

In a first preferred embodiment y has a value ranging from 0.005 to 0.16, z has a value ranging from 0.39 to 0.55 and k has a value ranging from 0.37 to 0.54.

In a second preferred embodiment y has a value ranging from 0.011 to 0.16, z has a value ranging from 0.39 to 0.55 and k has a value ranging from 0.37 to 0.54.

In a third preferred embodiment y has a value ranging from 0.011 to 0.14, z has a value ranging from 0.40 to 0.55 and k has a value ranging from 0.38 to 0.54.

The values of y, z and k in the advantageous, first, second and third embodiments described above are obtained by using the ingredients ratios described respectively in the advantageous, first, second and third embodiments of the method described above.

All the conditions already cited above relating to the synthesis of the MeAPO apply to said other embodiment of the invention.

As regards the mixture of (A) and MeAPO, it can be made by co-synthesis procedure (synthesis of MeAPO-(A) composites materials) optionally followed by formulation into a catalyst. The mixture of (A) and MeAPO can be used as itself as a catalyst. In another embodiment it can be formulated into a catalyst by combining with other materials that provide additional hardness or catalytic activity to the finished catalyst product. Materials which can be blended with the mixture of (A) and MeAPO can be various inert or catalytically active materials, or various binder materials. These materials include compositions such as kaolin and other clays, various forms of rare earth metals, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried powder. The amount of mixture of (A) and MeAPO which is contained in the final catalyst product ranges from 10 to 90 weight percent of the total catalyst, preferably 20 to 70 weight percent of the total catalyst.

The mixture of (A) and MeAPO can also be made by co-formulation procedure (blending of the separately synthesized (A) and MeAPO) optionally followed by combination with a binder. This mixture of (A) and MeAPO can be used as itself as a catalyst. In another embodiment it can be formulated into a catalyst by combining with other materials that provide additional hardness or catalytic activity to the finished catalyst product. The details are the same as above.

The mixture of (A) and MeAPO can also be made by blending of MeAPO and (A), at least one of (A) and the MeAPO has been combined with a binder prior to the blending. The obtained mixture can be used as itself as a catalyst. In another embodiment it can be formulated into a catalyst by combining with other materials that provide additional hardness or catalytic activity to the finished catalyst product. The details are the same as above.

With regards to the XTO process, the catalyst consisting of the mixture of (A) and MeAPO of the invention or the catalyst comprising the mixture of (A) and MeAPO of the invention is particularly suited for the catalytic conversion of oxygen-containing, halogenide-containing or sulphur-containing organic compounds to hydrocarbons. Accordingly, the present invention also relates to a method for making an olefin product from an oxygen-containing, halogenide-containing or sulphur-containing organic feedstock wherein said oxygen-containing, halogenide-containing or sulphur-containing organic feedstock is contacted with the above catalyst under conditions effective to convert the oxygen-containing, halogenide-containing or sulphur-containing organic feedstock to olefin products (the effluent of the XTO). Said effluent comprises light olefins and a heavy hydrocarbon fraction.

In this process a feedstock containing an oxygen-containing, halogenide-containing or sulphur-containing organic compound contacts the above described catalyst in a reaction zone of a reactor at conditions effective to produce light olefins, particularly ethylene and propylene. Typically, the oxygen-containing, halogenide-containing or sulphur-containing organic feedstock is contacted with the catalyst when the oxygen-containing, halogenide-containing or sulphur-containing organic compounds is in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 575° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, although a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. After a certain time on—stream the catalyst needs to be regenerated. This regeneration can be carried out in a separate reactor or in the same reactor. In case of a moving bed or fluidised bed reactor, a part of the catalyst is continuously or intermittently withdrawn from the conversion reactor and sent to a second reactor for regeneration. After the regeneration, the regenerated catalyst is continuously or intermittently sent back to the conversion reactor. In case of fixed bed reactor the reactor is taken off-line for regeneration. Generally this requires a second spare reactor that can take over the conversion into light olefins. After regeneration the fixed bed reactor is in stand-by until the spare reactor needs regeneration and the regenerated reactor takes over the conversion. Regeneration is carried out by injecting an oxygen-containing stream over the catalyst at sufficient high temperature to burn the deposited coke on the catalyst. The commercial scale reactor systems can be operated at a weight hourly space velocity (WHSV) of from 0.1 hr$^{-1}$ to 1000 hr$^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

The oxygenate feedstock is any feedstock containing a molecule or any chemical having at least an oxygen atom and capable, in the presence of the above MeAPO catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; diethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In XTO effluent among the olefins having 4 carbon atoms or more there are 50 to 85 weight % of butenes. More than 85% by weight and advantageously more than 95% of the hydrocarbons having 4 carbon atoms or more are C4 to C8 olefins.

According to an advantageous embodiment of the invention said olefin products (the effluent of the XTO) are fractionated to form a stream comprising essentially ethylene and at least a part of said stream is recycled on the catalyst to increase the propylene production and then the flexibility of ethylene vs propylene production. Advantageously the ratio of ethylene to the oxygen-containing, halogenide-containing or sulphur-containing organic feedstock is 1.8 or less.

The present invention also relates to a process (hereunder referred as "combined XTO and OCP process") to make light olefins from an oxygen-containing, halogenide-containing or sulphur-containing organic feedstock comprising:
contacting said oxygen-containing, halogenide-containing or sulphur-containing organic feedstock in the MTO reactor with the above catalyst at conditions effective to convert at least a portion of the feedstock to form an MTO reactor effluent comprising light olefins and a heavy hydrocarbon fraction;
separating said light olefins from said heavy hydrocarbon fraction;
contacting said heavy hydrocarbon fraction in the OCP reactor at conditions effective to convert at least a portion of said heavy hydrocarbon fraction to light olefins.

The effluent of the XTO reactor comprising light olefins and a heavy hydrocarbon fraction is sent to a fractionation section to separate said light olefins from said heavy hydrocarbon fraction. With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. It is desirable to have a substantially 100% conversion of the organic compound in the primary reactor. This conversion rate is adjusted by optimization of contact time and the frequency of regeneration of the catalyst.

With regards to the OCP process, said process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention.

The heavy hydrocarbon fraction produced in the XTO reactor is converted in the OCP reactor, also called an "olefin cracking reactor" herein, to produce additional amounts of ethylene and propylene. Advantageously the catalysts found to produce this conversion comprise a crystalline silicate of the MFI family which may be a zeolite, a silicalite or any other silicate in that family or the MEL family which may be a zeolite or any other silicate in that family. These catalysts have been described above in the description of (A).

The crystalline silicate catalyst has structural and chemical properties and is employed under particular reaction conditions whereby the catalytic cracking of the $C_4^+$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefinic catalytic cracking may be understood to comprise a process yielding shorter molecules via bond breakage. With such high silicon/aluminum ratio in the crystalline silicate catalyst, a stable olefin conversion can be achieved with a high propylene yield on an olefin basis.

The MFI catalyst having a high silicon/aluminum atomic ratio for use in the OCP reactor of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefin cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed there from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, spheres, extruded into other shapes, or formed into a spray-dried powder. In the catalytic cracking process of the OCP reactor, the process conditions are selected in order to provide high selectivity towards propylene or ethylene, as desired, a stable olefin conversion over time, and a stable olefinic product distribution in the effluent. Such objectives are favored by the use of a low acid density in the catalyst (i.e. a high Si/Al atomic ratio) in conjunction with a low pressure, a high inlet temperature and a short contact time, all of which process parameters are interrelated and provide an overall cumulative effect. The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 5 to 30 $hr^{-1}$, preferably from 10 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° C. to 590° C., typically around 560° to 585° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The OCP reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst can be regenerated several times.

The OCP reactor effluent comprises methane, light olefins and hydrocarbons having 4 carbon atoms or more. Advantageously said OCP reactor effluent is sent to a fractionator and the light olefins are recovered. Advantageously the hydrocarbons having 4 carbon atoms or more are recycled at the inlet of the OCP reactor, optionally mixed with the heavy hydrocarbon recovered from the effluent of the XTO reactor. Advantageously, before recycling said hydrocarbons having 4 carbon atoms or more at the inlet of the OCP reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OCP reactor are treated in a common recovery section.

Optionally, in order to adjust the propylene to ethylene ratio of the whole process (XTO+OCP), ethylene in whole or in part can be recycled over the OCP reactor and advantageously converted into more propylene. This ethylene can either come from the fractionation section of the XTO reactor or from the fractionation section of the OCP reactor or from both the fractionation section of the XTO reactor and the fraction section of the OCP reactor or even from the optional common recovery section.

Optionally, in order to adjust the propylene to ethylene ratio of the whole process (XTO+OCP), ethylene in whole or in part can be recycled over the XTO reactor where it combines with the oxygen-containing, halogenide-containing or sulphur-containing organic feedstock to form more propylene. This ethylene can either come from the fractionation section of the XTO reactor or from the fractionation section of the OCP reactor or from both the fractionation section of the XTO reactor and the fraction section of the OCP reactor or even from the optional common recovery section.

These ways of operation allow to respond with the same equipment and catalyst to market propylene to ethylene demand.

The performance of the catalyst of the present invention is substantially better that the simple sum of individual component. This shows a synergy of two molecular sieves in XTO and very particular catalytic properties. The catalyst shows good behaviour in XTO process in terms of stability and C3/C2 ratio, propylene purity and heavy olefins production (higher C4+ olefin yield for recycling).

FIG. 1 illustrates a specific embodiment of the invention. The effluent of the XTO reactor is passed to a fractionator 11. The overhead, a C1-C3 fraction including the light olefins is sent via line 2 to a common recovery section (not shown). The bottoms (the heavy hydrocarbon fraction) are sent via line 3 to the OCP reactor. The effluent of the OCP reactor is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 at the inlet of the OCP reactor. The bottoms, hydrocarbons having substantially 6 carbon atoms or more, are purged via line 6.

Figure 2A:
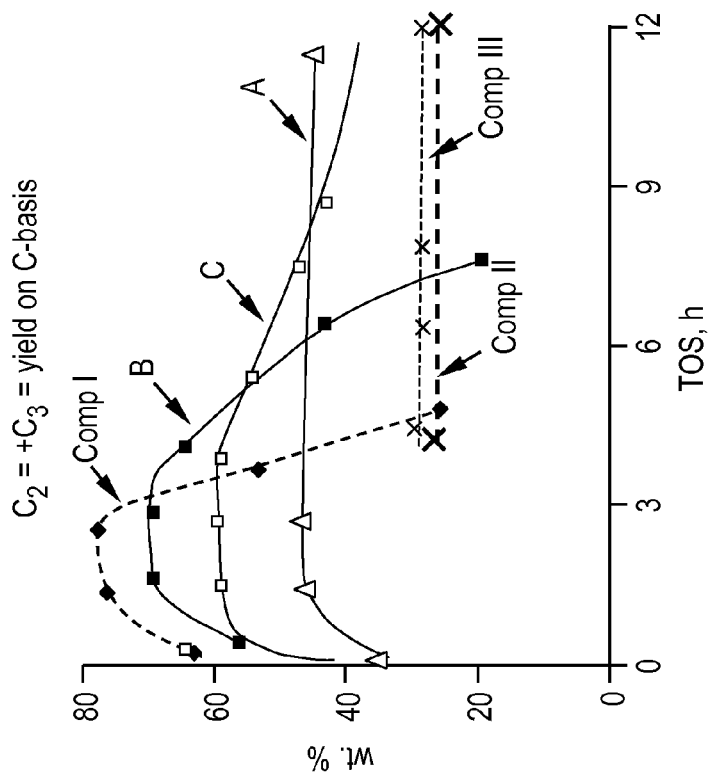
FIGS. 2A and 2B illustrate amount of light olefins produced versus on-stream time for catalysts in accordance with one or more embodiments.
Figure 2B:
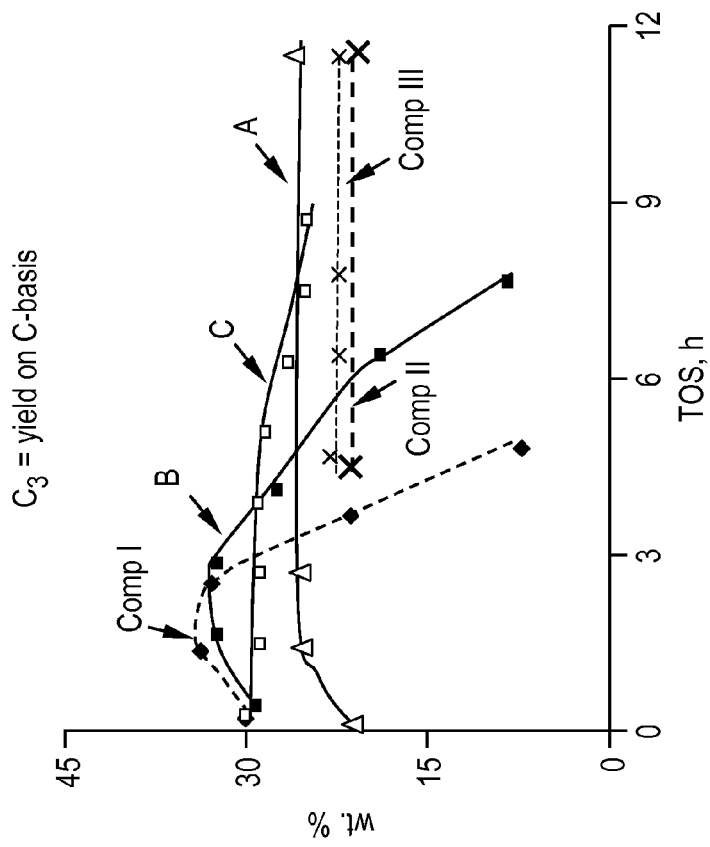

FIG. 2 illustrates the effect of the catalyst mixture. The catalyst mixtures (sample A, B, C and D) exhibit longer catalytic activity compared to SAPO-34 (sample COMP I) alone. These results indicate that the integrated amount of light olefins produced over the catalyst mixture is higher than over the SAPO-34 alone allowing to operate an industrial unit at higher space velocity and longer on-stream time and hence requiring lower regeneration frequency.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized to form polyolefins, particularly polyethylenes and polypropylenes. The present invention relates also to said polyethylenes and polypropylenes.

EXAMPLES

Example 1

A sample of SAPO-34 from Customec® showed molar Si content (Si/Si+Al+P)=0.041 and represents cubic crystal morphology with the average size 0.4 μm. The sample is hereinafter identified as comparative I.

Example 2

A sample of silicalite S-115 with atomic ratio Si/Al=150 has been obtained from UOP.
The sample is hereinafter identified as comparative II.

Example 3

A sample of silicalite S-115 with atomic ratio Si/Al=150 has been obtained from UOP. This sample was extruded (zeolite to binder ratio 80:20). The extrudates were dried at 110°

C. and then calcined at the temperature of 600° C. for a period of 10 h. Thereafter the resultant silicalite catalyst formulated with the binder was subjected to a steam treatment for 48 h at 550° C. Then the extrudates was exchanged with 0.1M $HNO_3$ (4.2 ml/1 g zeolite) at reflux condition, washed with distilled water and calcined at 400° C.

The sample is hereinafter identified as comparative III.

Example 4

A sample of zeolite ZSM-5 with Si/Al=13 in H-form synthesized without template has been obtained from TRICAT. This zeolite was steamed at 550° C. for 48 h. Steamed solid was treated by 3.14M solution of H3PO4 for 18 h under reflux condition (4.2 ml/1 g zeolite). Then the solid was separated by filtering from the solution. Obtained solid was dried at 110° C. for 16 h and calcined at 400° C. for 10 h. Final zeolite contained 5.6 wt. % of P and had atomic ratio Si/Al=25.

Example 5

Sample identified hereinafter as A was prepared by a mechanical mixture of 90 wt % of the solid described in example 1 and 10 wt % of the solid described in the example 2.

Example 6

Sample identified hereinafter as B and D were prepared by a mechanical mixture of 95 and 90 wt % of the solid described in example 1 and 5 and 10 wt % of the solid described in the example 3 respectively.

Example 7

Sample identified hereinafter as C was prepared by a mechanical mixture of 90 wt % of the solid described in example 1 and 10 wt % of the solid described in the example 4.

Example 8

XTO Conditions

Catalyst tests were performed on 2 g catalyst samples with a pure methanol feed at 450° C. (P=0.5 barg, WHSV=1.6 $h^{-1}$), in a fixed-bed, down flow stainless-steel reactor. Catalyst powders was pressed into wafers and crushed to 35-45 mesh particles. Prior to catalytic run all catalysts were heated in flowing $N_2$ (5 Nl/h) up to the reaction temperature. Analysis of the products was performed on-line by a gas chromatograph equipped with a capillary column. Catalytic performances of MeAPOs molecular sieves were compared at 100% of methanol conversion and maximum of catalyst activity. The results are on a carbon free basis.
OCP Conditions The feedstock which contains substantially non cyclic olefins C4+ (the heavy hydrocarbon fraction) was subjected to catalytic cracking (the OCP reactor) in the presence of an aluminosilicate catalyst in a fixed bed reactor at 575° C., LHSV=10 $h^{-1}$, P=1.5 bara. This catalyst comprises a commercially available silicalite which had been subjected to a dealumination treatment by combination of steaming with acid treatment so as to provide Si/Al ratio ~250. A detailed procedure of catalyst preparation is described in above cited EP1194502 B1.

The OCP performance has been simulated using a mathematic model employing conversion factors deduced from numerous testing of different feedstocks. Based on the stream composition going to the OCP reactor and on the required purges an optimum stream of C4 and heaviers are recycled around the OCP reactor. The lines under "OCP feed non cyclic olefins C4+" display the heavy hydrocarbon flow rate sent to the OCP (the second reactor). The lines under "XTO+ OCP" display the ethylene and propylene produced by the combination of the primary reactor (XTO) and the second reactor (OCP). The results are in tables 1-3 and FIG. 2 hereunder. The columns, indicating "simulation" provides the weighted average of the experimental obtained results of the individual catalysts. It is clear from these experimental results that the simulation is significantly different from the experimental results on the catalyst mixture.

TABLE 1

| | Comp I<br>SAPO-34<br>100 wt % | Sample A<br>SAPO-34 + silicalite<br>90 wt % + 10 wt % | | Comp II<br>silicalite<br>100 wt % |
|---|---|---|---|---|
| | RUN | RUN | simulation | RUN |
| T. ° C. | 450 | 450 | | 450 |
| WHSV. $h^{-1}$ | 1.6 | 1.6 | | 1.6 |
| P. barg | 0.5 | 0.5 | | 0.5 |
| Paraffins | 8.4 | 11.2 | 9.8 | 22.5 |
| Olefins | 90.7 | 82.4 | 87.7 | 60.7 |
| Dienes | 0.5 | 0.4 | 0.5 | 0.3 |
| Aromatics | 0.3 | 6.0 | 1.9 | 16.4 |
| Purity C2's | 97.7 | 98.0 | 97.3 | 93.7 |
| Purity C3's | 97.8 | 96.1 | 96.3 | 82.4 |
| C3/C2 | 0.7 | 1.4 | 0.9 | 2.6 |
| C2 + C3 | 77.6 | 44.8 | 72.5 | 26.5 |
| ethylene | 44.8 | 18.8 | 41.1 | 7.3 |
| propylene | 32.7 | 26.1 | 31.4 | 19.2 |
| OCP feed non cyclic olefins C4+ | | | | |
| Σ olefins | 12.7 | 35.0 | 14.6 | 31.7 |
| XTO + OCP | | | | |
| ethylene | 46.6 | 23.9 | 43.2 | 11.9 |
| propylene | 40.1 | 46.5 | 39.9 | 37.7 |
| C3/C2 | 0.9 | 2.0 | 0.9 | 3.1 |
| C2 + C3 | 86.7 | 70.4 | 83.1 | 49.6 |

Example 9

Catalyst tests were performed under the same conditions as in the example 8. Again, the data illustrate that the experimental results obtained on the catalyst mixture are different from the simulations that was expected from the weighted average of the individual catalyst.

TABLE 2

| | Comp I<br>SAPO-<br>34<br>100<br>wt % | Sample B<br>SAPO-34 +<br>steamed<br>silicalite<br>95 wt % +<br>4 wt % | | Sample D<br>SAPO-34 +<br>steamed<br>silicalite<br>90 wt % +<br>8 wt % | | Comp III<br>steamed<br>silicalite<br>100 wt % |
|---|---|---|---|---|---|---|
| | RUN | RUN | simulation | RUN | simulation | RUN |
| T. ° C. | 450 | 450 | | 450 | | 450 |
| WHSV, $h^{-1}$ | 1.6 | 1.6 | | 1.6 | | 1.6 |
| P, barg | 0.5 | 0.5 | | 0.5 | | 0.5 |
| Paraffins | 8.4 | 5.1 | 8.9 | 6.5 | 8.2 | 20.1 |
| Olefins | 90.7 | 93.0 | 89.8 | 88.4 | 82.6 | 68.1 |
| Dienes | 0.5 | 0.4 | 0.5 | 0.5 | 0.5 | 0.4 |

TABLE 2-continued

|  | Comp I SAPO-34 100 wt % | Sample B SAPO-34 + steamed silicalite 95 wt % + 4 wt % | | Sample D SAPO-34 + steamed silicalite 90 wt % + 8 wt % | | Comp III steamed silicalite 100 wt % |
|---|---|---|---|---|---|---|
|  | RUN | RUN | simulation | RUN | simulation | RUN |
| Aromatics | 0.3 | 1.5 | 0.7 | 3.9 | 0.7 | 11.4 |
| Purity C2's | 97.7 | 99.0 | 97.7 | 97.7 | 89.9 | 97.4 |
| Purity C3's | 97.8 | 98.7 | 97.6 | 95.6 | 89.8 | 93.4 |
| C3/C2 | 0.7 | 0.9 | 0.8 | 0.9 | 0.8 | 3.6 |
| C2 + C3 | 77.6 | 69.8 | 75.7 | 53.1 | 69.6 | 30.0 |
| ethylene | 44.8 | 37.2 | 43.3 | 27.7 | 39.8 | 6.5 |
| propylene | 32.7 | 32.5 | 32.3 | 25.5 | 29.7 | 23.5 |
| OCP feed non cyclic olefins C4+ | | | | | | |
| Σ olefins XTO + OCP | 12.7 | 22.7 | 13.6 | 34.3 | 15.3 | 35.2 |
| ethylene | 46.6 | 40.5 | 44.9 | 32.7 | 42.1 | 11.6 |
| propylene | 40.1 | 45.8 | 40.4 | 45.6 | 38.7 | 44.1 |
| C3/C2 | 0.9 | 1.1 | 0.9 | 1.4 | 0.9 | 3.8 |
| C2 + C3 | 86.7 | 81.2 | 85.3 | 78.3 | 81 | 55.6 |

Example 10

Catalyst tests were performed under the same conditions as in the example 9. Again, the data illustrate that the experimental results obtained on the catalyst mixture are different from the simulations that was expected from the weighted average of the individual catalyst.

TABLE 3

|  | Comp I SAPO-34 100 wt % RUN | Sample C SAPO-34 + P-ZSM-5 90 wt % + 10 wt % RUN |
|---|---|---|
| T, ° C. | 450 | 450 |
| WHSV, h$^{-1}$ | 1.6 | 1.6 |
| P, barg | 0.5 | 0.5 |
| Paraffins | 8.4 | 6.5 |
| Olefins | 90.7 | 90.5 |
| Dienes | 0.5 | 0.6 |
| Aromatics | 0.3 | 2.5 |
| Purity C2's | 97.7 | 98.6 |
| Purity C3's | 97.8 | 98.5 |
| C3/C2 | 0.7 | 1.0 |
| C2 + C3 | 77.6 | 58.9 |
| ethylene | 44.8 | 30.1 |
| propylene | 32.7 | 28.8 |
| OCP feed non cyclic olefins C4+ | | |
| Σ olefins XTO + OCP | 12.7 | 30.6 |
| ethylene | 46.6 | 34.5 |
| propylene | 40.1 | 46.7 |
| C3/C2 | 0.9 | 1.4 |
| C2 + C3 | 86.7 | 81.2 |

Example 11

Catalyst tests were performed under the same conditions as in the example 8 (MTO conditions) except the test was stopped after the fixed time-on-stream and a carbon deposition on the catalysts was analysed by CHN method.

TABLE 4

|  | Comp I SAPO-34 100 wt % | | Sample D SAPO-34 + steamed silicalite 90 wt % + 8 wt % | | Comp III steamed silicalite 100 wt % |
|---|---|---|---|---|---|
|  | RUN | RUN | RUN | simulation | RUN |
| TOS, min | 150 | 220 | 220 | for 220 | 720 |
| C wt % | 13.6 | 15.8 | 7.6 | >14.2 | 0.5 |

The results on coke measurement also illustrate the invention that on catalyst mixture less coke is produced than what could be expected from the weighted average of the individual catalysts.

The invention claimed is:

1. A mixture comprising at least 1 wt. % and up to 8 wt. % of a material selected from group A and 99 to 72 wt. % of at least a MeAPO molecular sieve, wherein group A represents at least one medium or large pore crystalline silicoaluminate or silicoaluminate mesoporous molecular sieve;
    wherein the medium pore crystalline silicoaluminate is selected from the group consisting of MFI, FER and MEL;
    wherein the large pore crystalline silicoaluminate is selected from the group consisting of FAU, MOR, LTL, MAZ, MWW and BEA; and
    wherein the silicoaluminate mesoporous molecular sieves is MCM-41.

2. The mixture of claim 1, wherein the mixture comprises from 99 to 75% of the MeAPO molecular sieves.

3. The mixture of claim 1, wherein the mixture comprises from 99 to 85% of the MeAPO molecular sieves.

4. The mixture of claim 1, wherein the material selected from group A is the medium pore crystalline silicoaluminate molecular sieves that is ZSM-5, silicalite, ZSM-11, Boralite D or silicalite-2.

5. The mixture of claim 1, wherein the MeAPO molecular sieves have a structure CHA or AEI or a mixture thereof.

6. The mixture of claim 1, wherein the MeAPO molecular sieves have the structure SAPO 18 or SAPO 34 or a mixture thereof.

7. The mixture of claim 1, wherein MeAPO comprises an intergrown phase of two MeAPO having AEI and CHA framework types.

8. The mixture of claim 1, wherein the MeAPO molecular sieve has an empirical chemical composition on an anhydrous basis, after synthesis and calcination, expressed by the formula $H_xMe_yAl_zP_kO_2$ in which, $$y+z+k=1;$$

$$x<y;$$

y has a value ranging from 0.0008 to 0.4;
z has a value ranging from 0.25 to 0.67; and
k has a value ranging from 0.2 to 0.67.

9. The mixture of claim 8, wherein the MeAPO molecular sieve has a plate crystal morphology in which the width (W) and the thickness (T) are such that: W/T is ≥10.

10. The mixture of claim 9, wherein W/T ranges from 10 to 100.

11. The mixture of claim 9, wherein T ranges from 0.01 to 0.07 μm.

12. The mixture of claim 11, wherein T ranges from 0.04 to 0.07 μm.

13. The mixture of claim 1, wherein the MeAPO has been prepared by a method comprising:
forming a reaction mixture containing a texture influencing agent (TIA), an organic templating agent (TEMP), at least a reactive inorganic source of $MeO_2$ essentially insoluble in the TIA, reactive sources of $Al_2O_3$ and $P_2O_5$;
crystallizing the above reaction mixture thus formed until crystals of the metalloaluminophosphate are formed;
recovering a solid reaction product; washing the solid reaction product with water to remove the TIA; and
calcinating the solid reaction product to remove the organic template.

14. The mixture of claim 1, wherein the Me of the MeAPO comprises a metal selected from the group consisting of silicon, germanium, magnesium, zinc, iron, cobalt, nickel, manganese, chromium and mixtures thereof.

15. The mixture of claim 14, wherein the Me is silicium.

16. A catalyst comprising the mixture of claim 1.

17. A process for making an olefin product from an oxygen-containing, halogenide-containing or sulphur-containing organic feedstock wherein said oxygen-containing, halogenide-containing or sulphur-containing organic feedstock is contacted in a first reactor with the catalyst of claim 16 under conditions effective to convert the oxygen-containing, halogenide-containing or sulphur-containing organic feedstock to a first reactor effluent comprising olefin products.

18. The process of claim 17, wherein the first reactor effluent, comprising light olefins and a heavy hydrocarbon fraction, is sent to a first fractionator to separate the light olefins from the heavy hydrocarbon fraction; the heavy hydrocarbon fraction is recycled to the first reactor at conditions effective to convert at least a portion of the heavy hydrocarbon fraction to olefin products.

19. The process of claim 17, wherein the olefin products include ethylene and propylene and are fractionated to form a stream comprising ethylene and at least a part of the stream is recycled to the first reactor to increase the propylene production.

20. The process of claim 17, wherein the first reactor effluent comprising light olefins and a heavy hydrocarbon fraction is sent to a first fractionator to separate the light olefins from the heavy hydrocarbon fraction; and the heavy hydrocarbon fraction is sent to a second reactor at conditions effective to convert at least a portion of the heavy hydrocarbon fraction to light olefins.

21. The process of claim 20, wherein the second reactor effluent is sent to a second fractionator and the light olefins are recovered; and heavy hydrocarbons having 4 or more carbon atoms are recycled to the second reactor, and mixed with the heavy hydrocarbons recovered from the effluent of the first reactor.

22. The process of claim 21, wherein the heavy hydrocarbons having 4 or more carbon atoms are sent to a third fractionator to separate a heavy hydrocarbon stream comprising C6+ hydrocarbons prior to recycling to the second reactor.

23. The process of claim 21, wherein the olefin products include ethylene and propylene and in order to adjust the propylene to ethylene production ratio of the process, ethylene is recycled to the second reactor; the ethylene can come from the first fractionator or from the second fractionator, or from both the first and second fractionators, or from a common recovery section.

24. The process of claim 21, wherein the olefin products include ethylene and propylene and in order to adjust the propylene to ethylene production ratio of the process, ethylene is recycled to the first reactor; the ethylene can come from the first fractionator or from the second fractionator, or from both the first and second fractionators, or from a common recovery section.

25. The process of claim 17, wherein the olefin products include ethylene which is further polymerized with one or more comonomers.

26. The process of claim 17, wherein the olefin products include propylene which is further polymerized with one or more comonomers.

27. The mixture of claim 1, wherein the group A represents at least one medium pore crystalline silicoaluminate selected from the group consisting of MFI, FER and MEL, or a silicoaluminate mesoporous molecular sieve that is MCM-41.

28. The mixture of claim 1, wherein group A represents at least one medium pore crystalline silicoaluminate selected from the group consisting of MFI, FER and MEL.

* * * * *